United States Patent [19]

Toyokuni et al.

[11] Patent Number: 5,210,078
[45] Date of Patent: May 11, 1993

[54] TRIFLUOROMETHYL ANALOGS OF FUCOSE AND USES THEREOF

[75] Inventors: Tatsushi Toyokuni, Seattle; Sen-itiroh Hakomori, Mercer Island, both of Wash.

[73] Assignee: The Biomembrane Institute, Seattle, Wash.

[21] Appl. No.: 693,292

[22] Filed: Apr. 30, 1991

[51] Int. Cl.[5] .................. A61K 31/70; A61K 31/715; C07H 1/00
[52] U.S. Cl. ...................................... 514/54; 514/23; 536/122; 536/123; 536/53; 536/123.1
[58] Field of Search ................... 514/23, 54; 536/122, 536/123

[56] References Cited

U.S. PATENT DOCUMENTS 3,817,978  6/1974  Jenkins et al. .................. 536/122

OTHER PUBLICATIONS

Adachi et al., "Expression of Le$^y$ Antigen in Human Immunodeficiency Virus-Infected Human T Cell Lines and in Peripheral Lymphocytes of Patients with Acquired Immune Deficiency Syndrome (AIDS) and AIDS-Related Complex (ARC)," *J. Exp. Med.* 167:322, 1988.

Angyal and Pickles, "Equilibria Between Pyranoses and Furanoses II. Aldoses," *Aust. J. Chem.* 25:1695, 1972.

Angyal and Pickles, "Equilibria Between Pyranoses and Furanoses III. Deoxyaldoses, The Stability of Furanoses," *Aust. J. Chem.* 25:1711, 1972.

Brandley et al., "Carbohydrate Ligands of the LEC Cell Adhesion Molecules," *Cell*, 63:861, 1990.

Bundy and Peterson, "The Synthesis of 15-Deoxy-9,-11-(Epoxyimino) Prostaglandins-Potent Thromboxane Synthetase Inhibitors," *Tetrahedron Lett.* No. 1, p. 41, 1978.

Corey and Snider, "A Total Synthesis of (+)-Fumagilin," *J. Am. Chem. Soc.* 94:2549, 1972.

Eggens et al., "A Role of Carbohydrate-Carbohydrate Interaction in the Process of Specific Cell Recognition During Embyrogenesis and Organogenesis: A Preliminary Note," *Biochem. Biophys. Res. Commun.* 158:913, 1989.

Eggens et al., "Specific Interaction Between Le$^x$ and Le$^x$ Determinants," *J. Biol. Chem.* 264:9476, 1989.

Gabius and Gabius, "Tumorlektinologie—Status und Perspektiven Klinischer Anwendung," *Naturwissenschaften* 77:505, 1990.

Hakomori, "Aberrant Glycosylation in Tumors and Tumor-Associated Carbohydrate Antigens," *Adv. Cancer Res.* 52:257, 1989.

Hakomori, "Glycosphingolipids in Cellular Interaction, Differentiation, and Oncogenesis," *Annu. Rev. Biochem.* 50:733, 1981.

Hindsgaul et al., "Synthesis of Type 2 Human Blood Group Antigenic Determinants. The H, X, and Y Haptens and Variations of the H Type 2 Determinant as Probes for the Combining Site of the Lectin I of Ulex europaeus," *Carbohydr. Res.* 109:109, 1982.

Hurst and McInnes, "The Alcoholysis of Trialkalkoxysilanes," *Can. J. Chem* 43:2004, 1965.

(List continued on next page.)

Primary Examiner—Johnnie R. Brown
Assistant Examiner—Everett White
Attorney, Agent, or Firm—Seed and Berry

[57] ABSTRACT

The present invention discloses trifluorofucoses and methods of making the same. Also disclosed are trifluorofucose analogs of fucose-containing oligosaccharides, and conjugates of trifluorofucose. Compositions are prepared which combine the trifluorofucose-containing oligosaccharides or trifluorofucose conjugates of the present invention with a pharmaceutically acceptable carrier or diluent. Tumor cell metastasis, autoimmune responses or inhibition of an inflammatory process may be inhibited by such compositions.

6 Claims, 5 Drawing Sheets

OTHER PUBLICATIONS

Jacquinet and Sinay, "Synthesis of Blood-Group Substances. Part 7. Synthesis of the Branched Trisaccharide O-αL-Fucopyranosyl-(1→3)-[O-β-D-galatopyranosyl-(1→4)-2-acetamido-2-deoxy-D-glucopyranose," *J. Chem. Soc., Perkin Trans.* 1:314, 1979.

Kameyama et al., "Total Synthesis of Sialyl Lewis X," *Carbohydr. Res.* 209:C1, 1991.

Koike et al., "An Efficient Synthesis of Ceramide from D-Glucose," *Glycoconjugate J.* 1:107, 1984.

Kojima and Hakomori, "Specific Interaction Between Gangliotriaosylceramide (Gg3) and Sialosyllactosylceramide ($G_{M3}$) as A Basis for Specific Cellular Recognition Between Lymphoma and Melanoma Cells," *J. Biol. Chem.* 264:20159, 1989.

Krishnamurti et al., "Preparation of Trifluoromethyl and Other Perfluoroalkyl Compounds with (Perfluoralkyl)trimethylsilanes," *J. Org. Chem.* 56:984, 1991.

Kristen et al., "Introduction of a New Selective Oxidation Procedure Into Carbohydrate Chemistry—An Efficient Conversion of D-Galactose Into L-Fucose," *J. Carbohydr. Chem.* 7:277, 1988.

Lonn, "Synthesis of a Tetra- and a Nona-Saccharide Which Contain α-L-Fucopyranosyl Groups and are Part of the Complex Type of Carbohydrate Moiety of Glycoproteins," *Carbohydr. Res.* 139:115, 1985.

Mahrwald et al., "The Oxidation of Primary Trimethylsilyl Ethers to Aldehydes-a Selective Conversion of a Primary Hydroxy Group into an Aldehyde Group in the Presence of a Secondary Hydroxy Group," *J. Prakt. Chem.* 328:777, 1986.

Matsushita et al., "Sialyl-Dimeric Lewis-X Antigen Expressed on Mucin-Like Glycoproteins in Colorectal Cancer Metastases," *Laboratory Invest.* 63:780, 1990.

Misevic et al., "Involvement of Carbohydrates as Multiple Low Affinity Interaction Sites in the Self-Association of the Aggregation Factor from the Marine Sponge Microciona prolifera," *J. Biol. Chem.* 262:5870, 1987.

Nicolaou et al., "Total Synthesis of the Tumor-Associated $Le^x$ Family of Glycosphingolipids," *J. Am. Chem. Soc.* 112:3693, 1990.

Nilsson et al., "Synthesis of a Dimeric Lewis X Hexasaccharide Derivative Corresponding to a Tumor-Associated Glycolipid," *Carbohydr. Res.* 183:71, 1988.

Phillips et al., "ELAM-1 Mediates Cell Adhesion by Recognition of a Carbohydrate Ligand, Sialyl-$Le^x$," *Science* 250:1130, 1990.

Prakash et al., "Fluoride-Induced Trifluoromethylation of Carbonyl Compounds with Trifluoromethyltrimethylsilane ($TMS-CF_3$). A Trifluoromethide Equivalent," *J. Am. Chem. Soc.* 111:393, 1989.

Sato et al., "Total Synthesis of X Hapten, $III^3$-Fucα-nLc4 Cer," *Carbohydr. Res.* 167:197, 1987.

Sato et al., "A Total Synthesis of Dimeric $Le^x$ Antigen, $III^3V^3Fuc_2nLc_6$Cer: Pivaloyl Auxiliary for Stereocontrolled Glycosylation)," *Tetrahedron Lett.* 29:5267, 1988.

Schmidt et al., "Stereospecific Synthesis of α-and β-L-Fucopyranosyl Phosphates and of GDP-Fucose via Trichloroacetimidate," *Liebigs Ann. Chem.* 121, 1991.

Sufrin et al., "Halogenated L-Fucose and D-Galactose Analogues: Synthesis and Metabolic Effects," *J. Med. Chem.* 23:143, 1980.

Taki et al., "Glycolipids of Metastatic Tissue in Liver From Colon Cancer: Appearance of Sialylated $Le^x$ and $Le^x$ Lipids," *J. Biochem.* 103:998, 1988.

Wolfrom and Moody, "Acyclic Derivatives of d-Lyxose," *J. Am. Chem. Soc.* 62:3465, 1940.

Yano et al., "The CH-Surface Area of Sugar Molecules as a Measure of Their Potential Hydrophobicity," *Bull. Chem. Soc. Jpn.* 61:2963, 1988.

TRIFLUOROMETHYL ANALOGS OF FUCOSE AND USES THEREOF

TECHNICAL FIELD

The present invention relates generally to trifluorofucose and methods of making and using the same. This invention is more particularly related to 6,6,6-trifluorofucose, methods of making the trifluorofucose, conjugates formed therefrom, trifluorofucose analogs of fucose-containing oligosaccharides, and methods for using these analogs and conjugates.

BACKGROUND OF THE INVENTION

Although the existence of glycoproteins (i.e., carbohydrate-containing proteins) and glycolipids (i.e., carbohydrate-containing lipids) as subclasses of proteins and lipids, respectively, has been known for some time, the initial understanding of the importance of the carbohydrate (also known as "oligosaccharide") portion of these molecules has been more recent. Carbohydrates have been implicated as crucial structures involved in numerous biological processes. The carbohydrate interaction may be with amino acid sequences (e.g., lectin motifs in a protein) or carbohydrates. Examples of biological processes in which carbohydrates are important include tumor cell metastasis, inflammatory processes and autoimmune responses.

Due to the difficulties in current approaches to modification (e.g., inhibition) of biological processes involving carbohydrate structures, there is a need in the art for improved methods and compositions to effect such modifications. The present invention fills this need, and further provides other related advantages.

SUMMARY OF THE INVENTION

Briefly stated, the present invention provides trifluorofucose, methods of making trifluorofucose, a variety of trifluorofucose analogs of fucose-containing oligosaccharides and conjugates of trifluorofucose, and methods of using such analogs and conjugates. In one aspect, the present invention provides a compound having the formula:

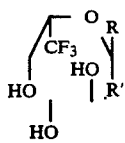

wherein R and R' are H or OH, but are not both H or both OH.

In another aspect of the present invention, methods for the synthesis of 6,6,6-trifluorofucose are disclosed. In one embodiment, the method comprises the steps of: (a) reacting a perbenzylated acyclic aldehyde derivative of lyxose with trifluoromethyltrimethylsilane to form trifluoromethylated siloxy adducts of lyxose; (b) hydrolyzing the siloxy adducts with about 1M hydrochloric acid to form desilylated adducts; (c) reducing the desilylated adducts by catalytic hydrogenation with palladium hydroxide to form deperbenzylated alcohols; (d) subjecting the alcohols to pertrimethylsilylation to form trimethylsiloxy adducts; (e) oxidizing the trimethylsiloxy adducts with Collins reagent to form trimethylsiloxy aldehydes; (f) desilylating the trimethylsiloxy aldehydes to form a mixture of 6,6,6-trifluorofucose and 6-deoxy-6,6,6-trifluoroaltrose; and (g) separating the fucose from the altrose.

Another aspect of the invention provides trifluorofucose analogs of fucose-containing oligosaccharides comprising Le$^x$, sialyl Le$^x$, disialyl Le$^x$, dimeric Le$^x$, sialyl-dimeric Le$^x$, trifucosyl Le$^x$, or Le$^y$, wherein at least one of the fucoses has been substituted with 6,6,6-trifluorofucose. Also provided are compositions comprising a trifluorofucose-containing oligosaccharide of the present invention in combination with a pharmaceutically acceptable carrier or diluent.

Within a related aspect, the present invention provides trifluorofucose conjugates. In one embodiment, the conjugate comprises a guanosine diphosphate (GDP) coupled to a compound having the formula:

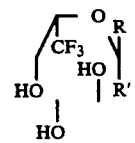

wherein R and R' are H or OH, but are not both H or both OH. Also provided are compositions comprising a conjugate of the present invention in combination with a pharmaceutically acceptable carrier or diluent.

Yet another aspect of the invention provides methods for using the trifluorofucose-containing oligosaccharides described above, the conjugates described above, or compositions including either. In one embodiment, a method for inhibiting the initiation of an inflammatory process is provided. The method comprises administering to a warm-blooded animal an effective amount of a composition of the present invention. In another embodiment, a method for inhibiting tumor cell metastasis is provided. The method comprises administering to a warm-blooded animal an effective amount of a composition of the present invention. In yet another embodiment, a method for inhibiting autoimmune responses is provided. The method comprises administering to a warm-blooded animal an effective amount of a composition of the present invention.

Within a related aspect, the present invention provides a method for inhibiting the enzyme GDP fucose: x-fucosyltransferase in a biological preparation. The method comprises contacting a biological preparation with an effective amount of a trifluorofucose-GDP conjugate described above.

These and other aspects of the present invention will become evident upon reference to the following detailed description and attached drawings.

DETAILED DESCRIPTION OF THE INVENTION

As noted above, the present invention is generally directed towards methods and compositions for the modification (e.g., inhibition) of biological processes involving fucose-containing carbohydrate structures. More specifically, the disclosure of the present invention shows that trifluoromethyl analogs of fucose may be substituted for fucose. Replacement of the methyl group with a trifluoromethyl group results in analogs of fucose which are more hydrophobic. Such analogs of fucose may be, for example, incorporated into oligosaccharides, or conjugated to non-saccharide molecules. Such oligosaccharide and non-saccharide molecules may be used for a variety of purposes, including to modify biological processes in vivo and in vitro.

Fucose is an important component of a number of crucial structures recognized by lectins, glycosyltransferases and carbohydrates themselves. For example, the fucose-containing oligosaccharide sialyl Le$^x$ appears to be involved in the recognition of lymphokine-induced lectins expressed by endothelial or platelet cells (Phillips et al., Science 250:1130, 1990). The initiation of an inflammatory process, i.e., recruitment of neutrophils to sites of inflammation, appears to be mediated by sialyl Le$^x$ structures found on cell-surface glycoprotein and glycolipid carbohydrate groups of neutrophils. The expression of another fucose-containing oligosaccharide, Le$^y$, in CD8+ T-cell populations correlates with various disease processes, including AIDS (Adachi et al., J. Exp. Med. 167:322, 1988). Other fucose-containing oligosaccharides, including Le$^x$ and sialyl-dimeric Le$^x$ (Taki et al., J. Biochem. 103:998, 1988; Matsushita et al., Laboratory Invest. 63:780, 1990), appear to be associated with tumor cell metastasis.

The present invention provides trifluoromethyl analogs of fucose having the formula:

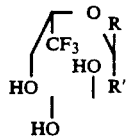

wherein R and R' are H or OH. As used herein, the formula depicted above represents both pyranose and furanose forms (i.e., 9a-Pα, 9a-Pβ, 9b-Fα and 9b-Fβ of FIG. 1).

Figure 1:
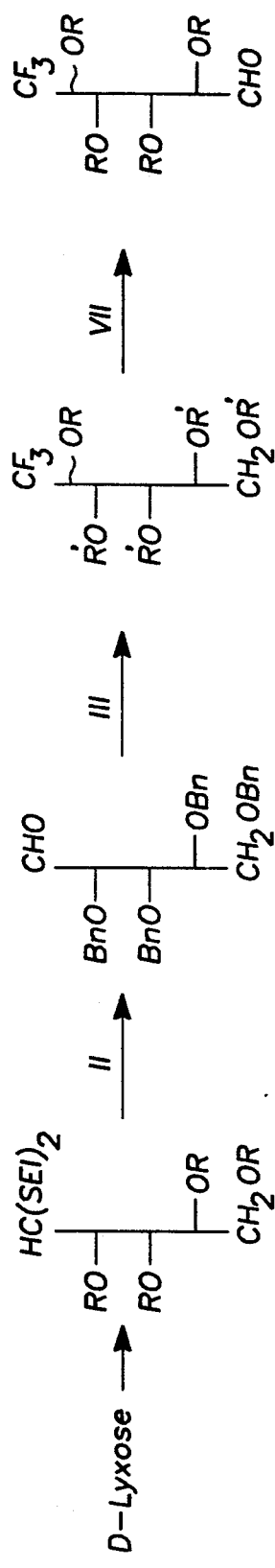
FIG. 1 depicts a flowchart illustrating a procedure for the synthesis of trifluoromethyl analogs of fucose and 6-deoxy-altrose. Reagents and conditions are as follows: i, BnBr, NaH, DMF, room temp, 3 h; ii, HgCl$_2$, CdCO$_3$, acetone-H$_2$O, room temp, 20 h; iii, TMS-CF$_3$, TBAF, THF, 0° C.→room temp, 2 h; iv, 1M HCl, room temp, 4 h; v, palladium hydroxide on carbon, H$_2$ (1 atm), room temp, 5 h; vi, Me$_3$SiCl, Me$_3$SiNHSiMe$_3$, pyr, room temp, 3 h; vii, CrO$_3$-pyr, CH$_2$Cl$_2$, 0° C.→room temp, 1 h; viii, MeOH—H$_2$O, reflux, 3 h.
Figure 1:
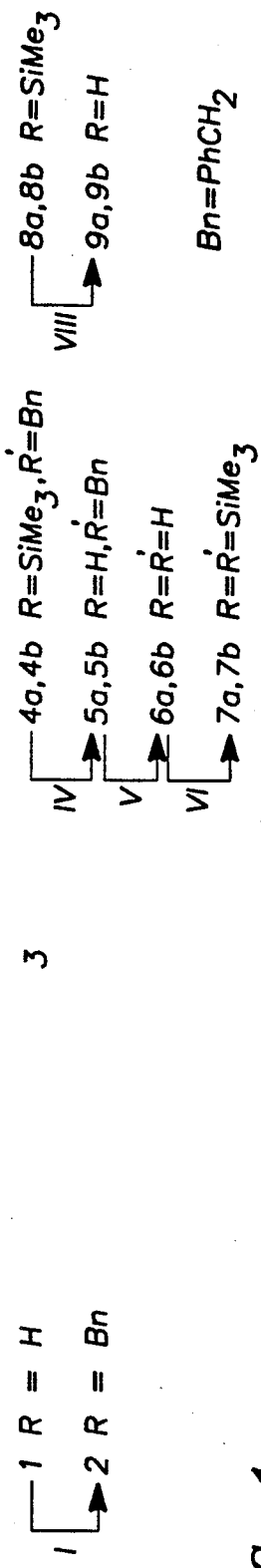
Figure 1:
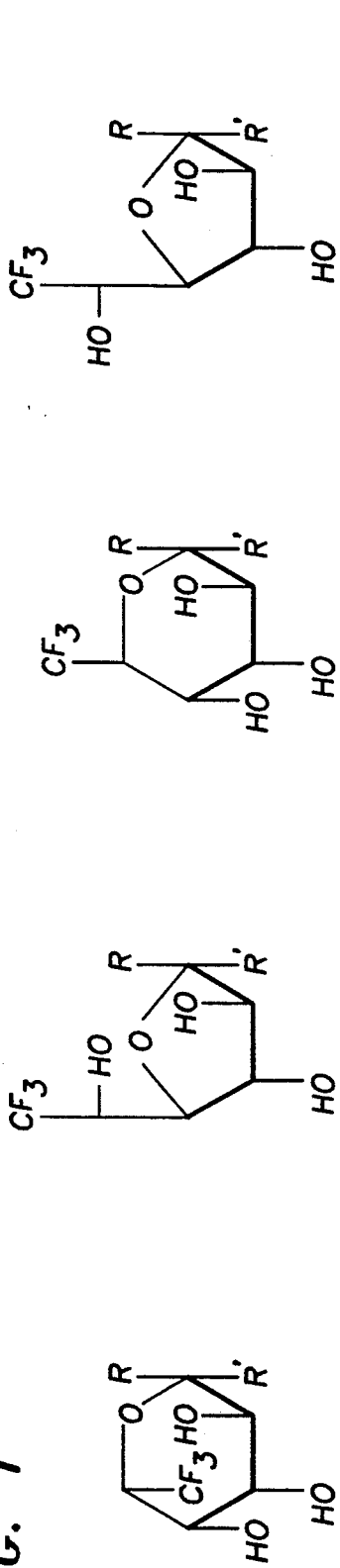
Figure 1:
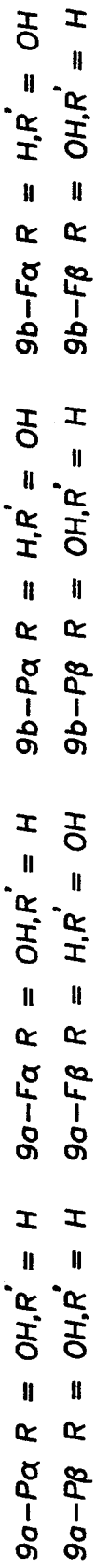
Figure 1:
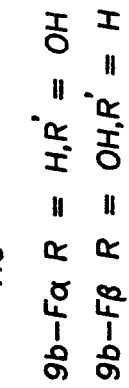

As disclosed within the present invention, trifluoromethyl analogs of fucose may be prepared by synthetic protocols which include the application of a nucleophilic trifluoromethylation reaction, e.g., using trifluoromethyltrimethylsilane (TMS-CF$_3$), to an acyclic sugar aldehyde (e.g., FIG. 1). In brief, a perbenzylated acyclic aldehyde derivative of lyxose is trifluoromethylated using TMS-CF$_3$ to produce trifluoromethylated siloxy adducts of lyxose. Subsequent hydrolysis, e.g., with 1M HCl, yields trifluoromethylated, desilylated adducts in which the alcohol adjacent to the trifluoromethyl group is unprotected. After catalytic hydrogenation, e.g., with palladium hydroxide, the resulting deperbenzylated alcohols are subjected to "Schick" oxidation (Mahrwald et al., J. Prakt. Chem. 328:777, 1986) in order to convert the primary hydroxyl group into the aldehyde. More specifically, the deperbenzylated alcohols are first subjected to pertrimethylsilylation to form trimethylsiloxy adducts. The adducts are then oxidized with Collins reagent to form trimethylsiloxy aldehydes (i.e., the primary alcohol has been converted to the aldehyde and the other alcohols remain silylated). Desilation, e.g., with aqueous methanol under reflux, yields a mixture of the trifluoromethyl analogs of fucose and 6-deoxy-altrose. The analogs may be isolated using routine separation techniques, e.g., silica gel chromatography. It will be appreciated by those skilled in the art that individual steps may be modified, such as by substituting reagents, without significantly deviating from the overall reaction pathway provided by the present invention. For example, in addition to the use of 1M HCl, trimethylsilyl ethers may be cleaved by n-Bu$_4$N$^+$F$^-$/THF (Corey and Snider, J. Am. Chem. Soc. 94:2549, 1972), K$_2$CO$_3$/dry MeOH (Hurst and McInnes, Can. J. Chem 43:2004, 1965) or citric acid/MeOH (Bundy and Peterson, Tetrahedron Lett. 41, 1978).

Within the present invention, trifluoromethyl analogs of fucose may be used in a variety of ways. For example, trifluorofucose may be incorporated into oligosaccharides, e.g., those which normally contain one or more fucose residues. Representative examples of fucose-containing oligosaccharides include Le$^x$, sialyl Le$^x$, dimeric Le$^x$, sialyl-dimeric Le$^x$, trifucosyl Le$^x$, and Le$^y$, whose structures are shown below. Depending upon the identity of R, an oligosaccharide may be the entire structure or may be a portion of a larger structure. For example, where R is a hydroxyl group, the oligosaccharide contains only carbohydrate sequences. Where R is one or more amino acid residues, the oligosaccharide is within a glycopeptide, glycopolypeptide or glycoprotein. Oligosaccharides are typically linked to amino acids via the hydroxyl group of a serine or threonine residue. Where R is a lipid, the oligosaccharide is within a glycolipid. Typical lipids include ceramides, i.e., sphingolipid bases which are acylated on the amine with a fatty acid.

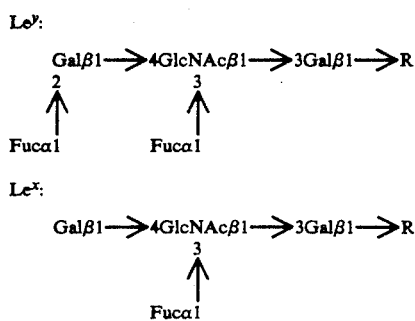

-continued

Sialosyl-Le$^x$:

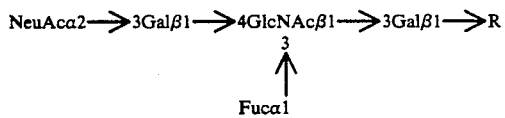

Sialosyl-dimeric Le$^x$:

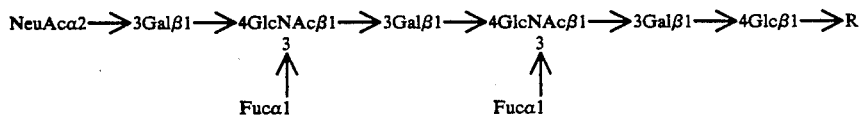

Dimeric Le$^x$:

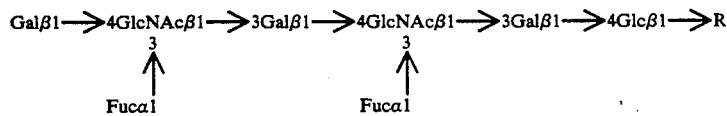

Trifucosyl Le$^x$:

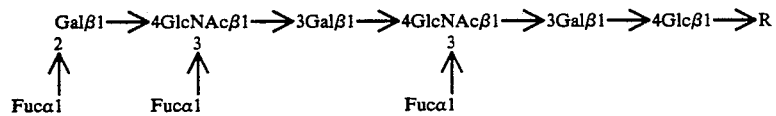

Where an oligosaccharide contains more than one fucose, one or more selected fucose residues or all of the fucose residues may be replaced with trifluorofucose. Numerous methods for preparing oligosaccharides, glycolipids and glycopeptides are known to those skilled in the art. Given the teachings provided herein, it would be evident that such methods may be readily modified to incorporate one or more trifluoromethyl fucose analogs of the present invention.

Trifluorofucose may also be covalently linked to non-saccharide molecules, e.g., guanosine diphosphate (GDP) to form a trifluorofucose-GDP conjugate. Conjugates of the present invention are typically produced by coupling via R' of the trifluoromethyl fucose analogs described above. GDP fucose is the natural substrate for GDP fucose: x-fucosyltransferase, the enzyme essential for making various fucose-containing structures. A trifluorofucose-GDP conjugate may be used to inhibit this enzyme and its synthesis of fucose-containing structures. For example, blood cell expression of Le$^x$ or sialyl Le$^x$ may be inhibited by such conjugates.

Compositions may be prepared which combine the trifluorofucose-containing oligosaccharides or trifluorofucose-GDP conjugates of the present invention with a pharmaceutically acceptable carrier or diluent. Suitable carriers or diluents include physiological saline. It will be recognized by one skilled in the art that the composition may be prepared in sterile form.

As noted above, the trifluorofucose-containing oligosaccharides and trifluorofucose-GDP conjugates of the present invention may be used, individually or collectively, in a variety of methods to modify (e.g., inhibit) biological processes involving fucose-containing carbohydrate structures. For example, the compositions described above may be administered to a warm-blooded animal, such as a human, to inhibit the initiation of an inflammatory process. Alternatively, such compositions may be administered to inhibit tumor cell metastasis or to inhibit autoimmune responses. Given the teachings provided herein, it would be evident to those skilled in the art that compounds, oligosaccharides and/or conjugates of the present invention may be useful in connection with other biological processes, known or found, to involve fucose-containing carbohydrate structures. Oligosaccharide-containing compositions will generally be administered at a concentration of about 0.1 to 1M and typically at about 0.2 to 0.5M. It will be evident to those skilled in the art how to determine the optimal effective dose for a particular composition (e.g., based upon in vitro and in vivo studies in non-human animals), and that the number and frequency of administration will be dependent upon the response of the patient.

A variety of routes of administration may be used. Typically, administration will be intravenous or intracavitory, e.g., in pleural or peritoneal cavities, or in the bed of a resected tumor. A composition may be administered in combination with other agents, e.g., an immunotherapeutic or chemotherapeutic agent. When a combination of a composition of the present invention and such an agent is desired, each may be administered sequentially, simultaneously, or combined and administered as a single composition. Diagnostic techniques, such as CAT scans, may be performed prior to and subsequent to administration to confirm the effectiveness of the inhibition, e.g., of metastatic potential.

The trifluorofucose-containing oligosaccharides and trifluorofucose-GDP conjugates of the present invention may also be used, individually or collectively, for in vitro inhibition in a biological preparation. The term "biological preparation" includes biological samples taken in vivo and in vitro (either with or without subsequent manipulation), as well as those prepared synthetically. Representative examples of biological preparations include cells, tissues, solutions and bodily fluids, such as (or from) blood, urine, saliva, sweat, synovial, cerebrospinal and tears. A trifluorofucose-GDP conjugate, for example, may be added to a biological preparation containing GDP fucose: x-fucosyltransferase to inhibit the enzyme. Such inhibition has numerous uses, including studying the affect of inhibiting the expression of fucose-containing oligosaccharides in a particular cell system, such as primary or cultured tumor cells.

To summarize the examples which follow, Example 1 describes the synthesis of trifluoromethyl analog of L-Fucose and 6-Deoxy-D-Altrose; Example 2 describes the synthesis of trifluorofucose analog of Le[x]; and Example 3 describes the synthesis of trifluorofucose-GDP conjugate.

The following examples are offered by way of illustration and not by way of limitation.

EXAMPLES

Example 1

Synthesis of Trifluoromethyl Analog of L-Fucose and 6-Deoxy-D-Altrose

The reaction pathway is shown in FIG. 1 and is the source of the compound numbering system used hereinafter. All new compounds exhibited satisfactory spectral and high-resolution mass data.

The acyclic derivative D-lyxose, 3, was prepared from the known diethyl dithioacetal derivative (Wolfrom and Moody, *J. Am. Chem. Soc.* 62:3465, 1940; D-lyxose from Aldrich, Milwaukee, Wis.), 1, in an overall yield of 89% by sequential perbenzylation with benzyl bromide in the presence of sodium hydride (1→2) and dethioacetalization with mercuric chloride and calcium carbonate (2→3). Trifluoromethylation using TMS-CF3, prepared as reported (Prakash et al., *J. Am. Chem. Soc.* 111:393, 1989; Krishnamurti et al., *J. Org. Chem.* 56:984, 1991), was then carried out with 3 in the presence of a catalytic amount of tetrabutylammonium fluoride (TBAF) (Lancaster, Winham, N.H.), according to the conditions reported by Prakash et al., (*J. Am. Chem. Soc.* 111:393, 1989), yielding a mixture of trifluoromethylated siloxy adducts, 4a and 4b. Subsequent hydrolysis with 1M HCl gave a ca. 1:1 mixture of trifluoromethylated alcohols, 5a and 5b, in a 79% overall yield from 3. Column chromatography on silica gel (230–400 mesh, 7:1 hexane-acetone) resulted in a moderate separation of 5a ($R_f$, 0.26) and 5b ($R_f$, 0.21). 5a: $[\alpha]_D$ −22.3° (c 3.8, CHCl3), 5b: $[\alpha]_D$ −15.2° (c 3.7, CHCl3). Since the separation of these alcohols was found to be troublesome, the mixture of 5a and 5b was used for further reactions.

After catalytic hydrogenation with palladium hydroxide, the resulting alcohols, 6a and 6b, were subjected to Schick oxidation (Mahrwald et al., *J. Prakt. Chem.* 328:777, 1986) in order to convert the primary hydroxy group into the aldehyde. The reaction sequence (6a, 6b→7a, 7b→8a, 8b) was basically the same as reported (Kristen et al., *J. Carbohydr. Chem.* 7:277, 1988). Thus, pertrimethylsilylation, yielding 7a and 7b, followed by oxidation with Collins agent (CrO3-pyridine complex) afforded a mixture of trimethylsiloxy aldehydes, 8a and 8b. Desilylation with aqueous methanol under reflux for 3 h (Hurst and McInnes, *Can. J. Chem.* 43:2004, 1965), and subsequent column chromatography on silica gel (230–400 mesh, 20:1:0.1 EtOAc-EtOH—H2O) provided the trifluoromethyl analogue of L-fucose (9a) ($R_f$ 0.36) and of 6-deoxy-D-altrose (9b) ($R_f$ 0.51) in 38% and 36% overall yields, respectively, from the mixture of 7a and 7b. 9a: m.p. 122°-123°; $[\alpha]_D$ −36.5° (c 2.5, H2O, after 24 h); $^{19}$F NMR (CD3OD, CFCl3) δ−103.11 (d, J=7.0 Hz), −103.23 (d, J=8.5 Hz), −106.39 (d, J=8.5 Hz), and −106.42 (d, J=7.0 Hz); HREIMS 201.0363 (C6H8F3O4[M-OH]+, Δ1.2 mmu), 9b: syrup; $[\alpha]_D$ −1.3° (c 2.5, H2O, after 24 h); $^{19}$F NMR (CD3OD, CFCl3) δ−103.16 (d, J=9.0 Hz), −103.37 (d, J=6.5 Hz), −105.29 (d, J=6.5 Hz), and −105.06 (d, J=9.0 Hz); HREIMS 201.0365 (C6H8F3O4[M-OH]+, Δ1.0 mmu).

The $^1$H NMR spectra of 9a and 9b revealed an equilibrium mixture composed of two pyranoses (α, β) and two furanoses (α, β) (Table 1). The proportions of each form were found to be 29:43:11:17 (9a-Pα:9a-Pβ:9a-Fα:9a-Fβ) and 14:20:33:33 (9b-Pα:9b-Pβ:9b-Fα:9b-Fβ). The ratios for L-fucose and D-altrose were reported to be 28:67:5 (Pα:Pβ:Fα+Fβ) (Angyal and Pickles, *Aust. J. Chem.* 25:1695, 1972) and 30:41:18:11 (Pα:Pβ:Fα:Fβ) (Angyal and Pickles, *Aust. J. Chem.* 25:1711, 1972), respectively. It is worth noting that replacement of the methyl group with the trifluoromethyl group increases the furanose content, particularly for 9b which exists in the furanose form. The spectrum of crystalline 9a soon after dissolution showed a similar composition as at equilibrium, probably due to its rapid mutarotation.

TABLE 1

| | $^1$H NMR data[a] for 9a and 9b | | | | |
|---|---|---|---|---|---|
| | $\delta^b$, multiplicity[c], (J, Hz) | | | | |
| | H-1 | H-2 | H-3 | H-4 | H-5 |
| 9a-Pα | 5.32 d (3.5) | 3.79 dd (10.5, 3.5) | 3.84 dd (10.5, 3.0) | 4.23 d (3.0) | 4.51 q (7.0) |
| -Pβ | 4.65 d (8.0) | 3.50 dd (10.0, 8.0) | 3.63 dd (10.0, 3.5) | 4.18 d (3.5) | 4.10–4.25[d] |
| -Fβ | 5.26 d (5.0) | 4.06 dd (8.0, 5.0) | —[e] | —[e] | 4.10–4.25[d] |
| -Fβ | 5.20 d (3.5) | 3.97 dd (4.0, 3.5) | —[e] | —[e] | 4.10–4.25[d] |
| 9b-Pα | 5.03 d (3.0) | 3.82 dd (5.5, 3.0) | 3.93–3.96[d] | 4.11 dd (7.5, 3.5) | 4.49–4.41[d] |
| Pβ | 5.16 d (1.0) | 3.81 dd (4.0, 1.0) | 4.02–4.07[d] | —[e] | —[e] |
| Fα | 5.25 d (2.0) | 4.00 t (2.0) | 4.18–4.21[d] | 4.02–4.05[d] | 4.14–4.25[d] |
| Fβ | 5.28 d (4.5) | 4.05 dd (6.0, 4.5) | 4.29 t (6.0) | 3.94 dd (7.5, 6.0) | 4.14–4.25[d] |

[a] 500 MHz; D2O at 35°; after 24 h.
[b] In ppm downfield from sodium 3-(trimethylsilyl)propionate.
[c] d = doublet, dd = doublet of doublets; t = triplet, q = quartet.
[d] The peaks were overlapping and the assignments thus remained obscure.
[e] Not resolved.

Example 2

Synthesis of Trifluorofucose Analog of Le[x]

Synthetic studies toward the Lewis X (Le[x]) family of antigens have been reported by several groups: (a) Sialyl Le[x]: Kameyama et al., *Carbohydr. Res.* 209:Cl, 1991. (b) Monomeric, dimeric, and trimeric Le[x]: Nicolaou et al., *J. Am. Chem. Soc.* 112:3693, 1990. (c) Dimeric Le[x]: Sato et al., *Tetrahedron Lett.* 29:5267, 1988. (d) Monomeric Le[x]: Sato et al., *Carbohydr. Res.* 167:197, 1987. (e) Le[x] fragments: Nilsson et al., *Carbohydr. Res.* 183:71, 1988; Lonn, *Carbohydr. Res.* 139:115, 1985; Hindsgaul et al., *Carbohydr. Res.* 109:109, 1982; Jacquinet and Sinay, *J. Chem. Soc., Perkin Trans.* 1:314, 1979. Application of these methods produces trifluorofucose analogs of fucose-containing oligosaccharides by replacing a fucose residue with trifluorofucose in their synthetic schemes.

Figure 2A:
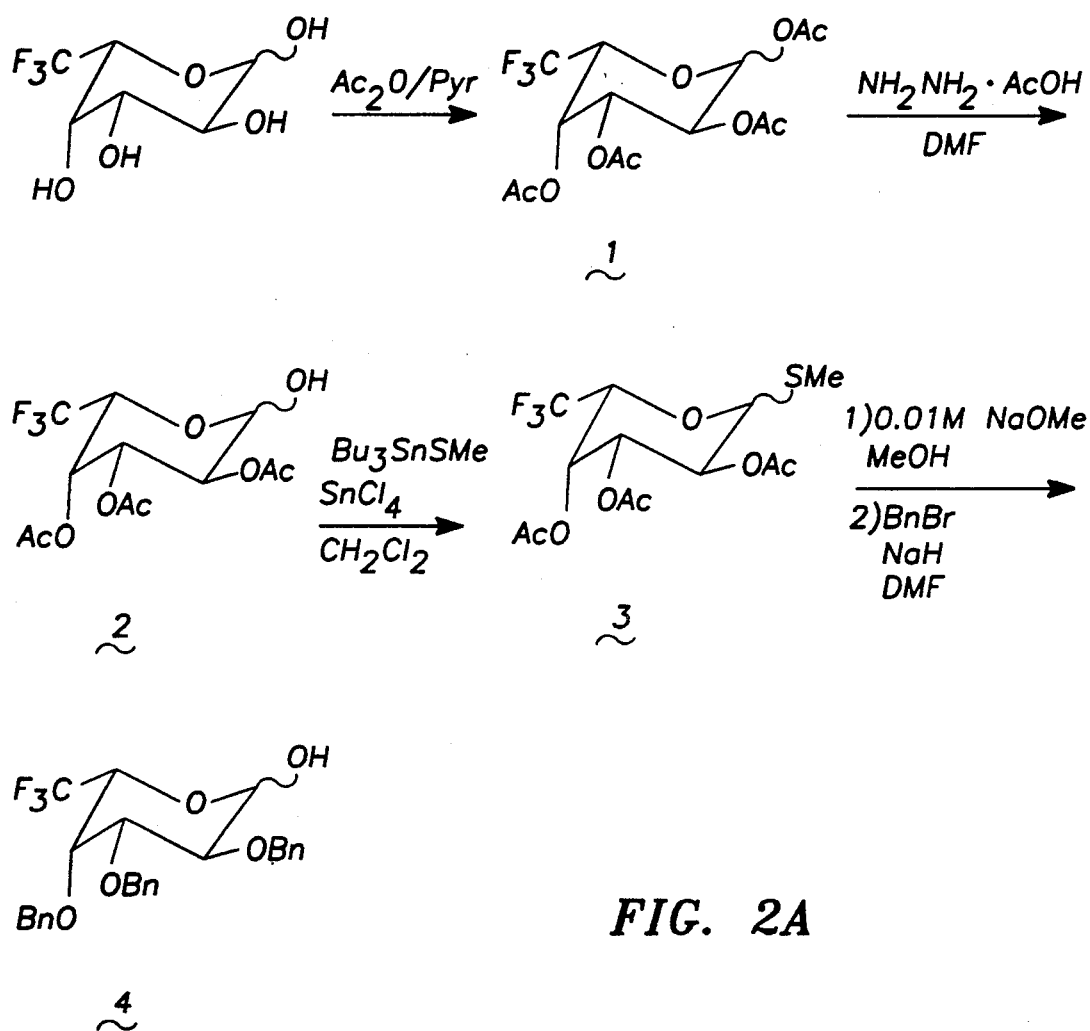
FIGS. 2A, 2B, and 2C depict a flowchart illustrating a procedure for the synthesis of a trifluorofucose analog of Le$^x$ ceramide.

For example, modification of the method for synthesizing Le$^x$, reported by Sato et al. (Sato et al., Carbohydr. Res. 167:197, 1987), by use of trifluorofucose yields a trifluorofucose analog of Le$^x$ (FIG. 2). Methyl 1-thiotrifluorofucoside 4 is prepared from trifluorofucose by a series of reactions shown in FIG. 2A. Acetylation of trifluorofucose with acetic anhydride and pyridine gives trifluorofucose acetate (1) (HRFABMS 327.0690 ($C_{12}H_{14}F_3O_7$ [M+H-AcOH]+, Δ0.2 mmu). Regioselective de-O-acetylation at C-1 by treatment of 1 with an equivalent amount of hydrazine acetate (1→2), followed by thiomethylation using tributyltin methylthiolate, produces a mixture of α and β methyl thiotrifluorofucoside 3. Treatment of 3 with 0.01M methanolic sodium methoxide and subsequent benzylation with benzyl bromide in the presence of sodium hydride gives a mixture of α and β methyl 1-thiotrifluorofucoside (4).

Figure 2B:
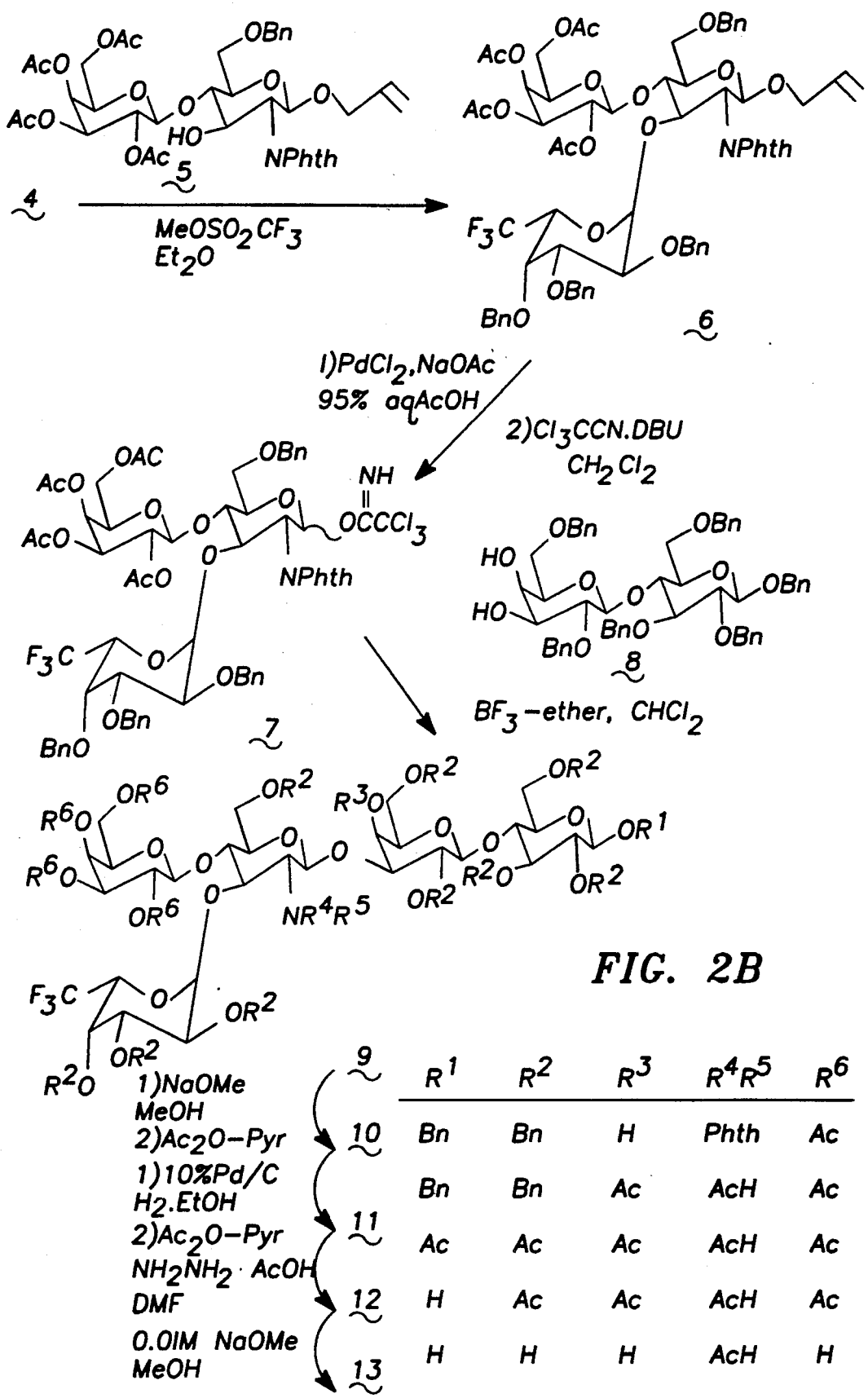

A trifluorofucosyl residue is then introduced by the reaction of 4 with the known disaccharide 5 (Sato et al., Carbohydr. Res. 167:197, 1987) in the presence of methyltriflate in ether (FIG. 2B). The resulting trisaccharide 6 is deallyated with palladium(II) chloride and sodium acetate in aq. acetic acid and then converted to its trichloroacetimidate 7 with trichlorocetonitrile and DBU for the further coupling reaction to lactoside derivative 8. The coupling reaction of 7 and 8 is accomplished by treating the mixture of 7 and 8 with boron trifluoride etherate in dichloromethane, producing pentasaccharide 9. Conventional protective-group modulation converts 9 sequentially to 10 (i. NaOMe, MeOH; ii. Ac$_2$O-Pyr), 11 (i. 10% Pd/C, EtOH, H$_2$ (1 atm); ii. Ac$_2$O-Pyr), 12 (NH$_2$NH$_2$ AcOH, DMF), and then trifluorofucose analog of lacto-N-fucopentaose III (13) (0.01M NaOMe, MeOH).

Figure 2C:
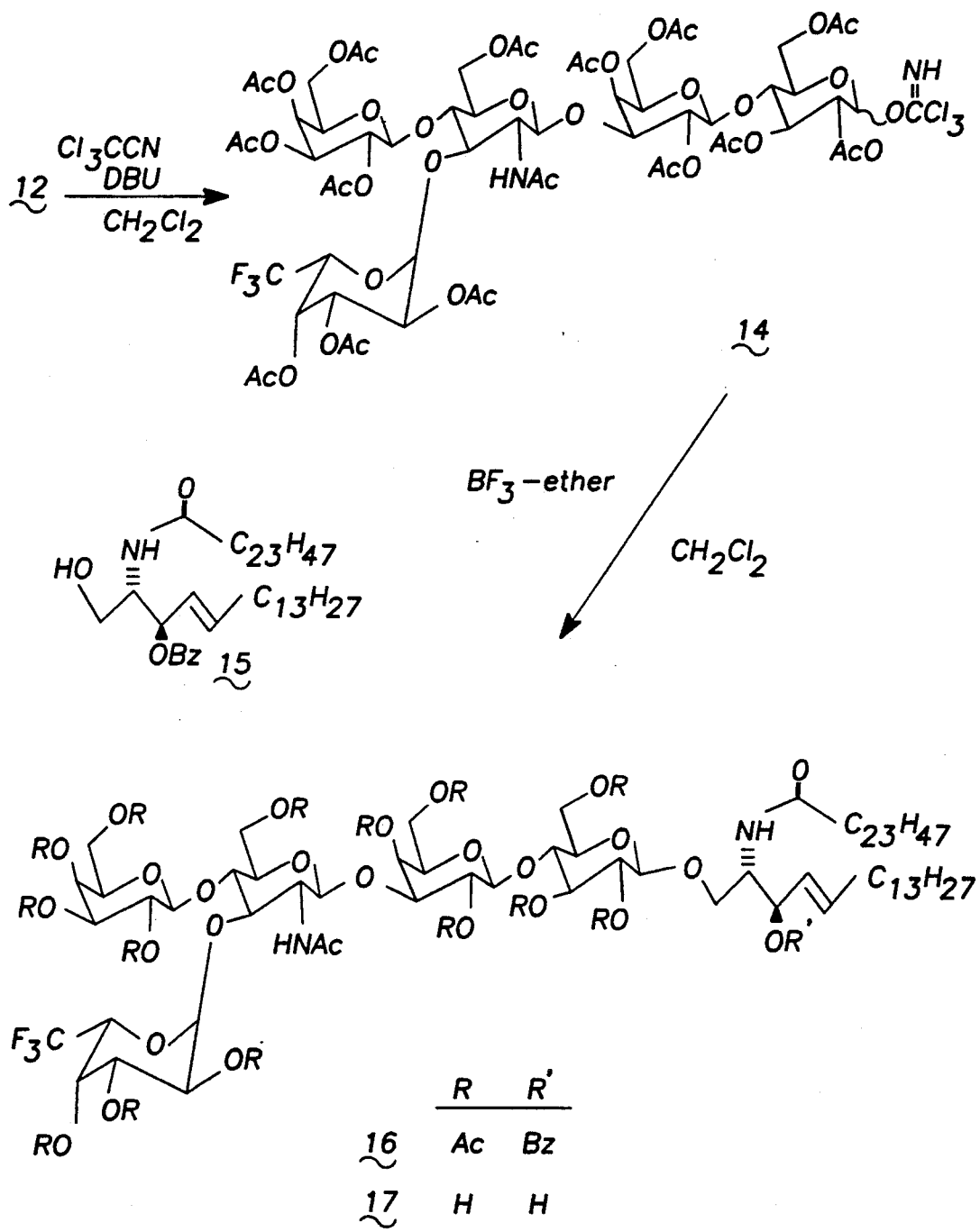

Pentasacchride hemiacetal 12 is a useful intermediate for the preparation of conjugates with amino acids, peptides, proteins, lipids, or polymer supports with or without a spacer arm. The coupling reaction to a ceramide derivative 15 (Koike et al., Glycoconjugate J. 1:107, 1984), shown in FIG. 2C, is one of the examples. Trichloroimidation of 12 with trichloroacetonitrile and DBU in CH$_2$Cl$_2$, followed by boron trifluoride etherate-catalyzed glycosylation, affords the protected Le$^x$ glycolipid analogue 16. Deacylation of 16 yields trifluorofucose analogue of Le$^x$ ceramide 17.

Example 3

Synthesis of Trifluorofucose-GDP Conjugate

Figure 3:
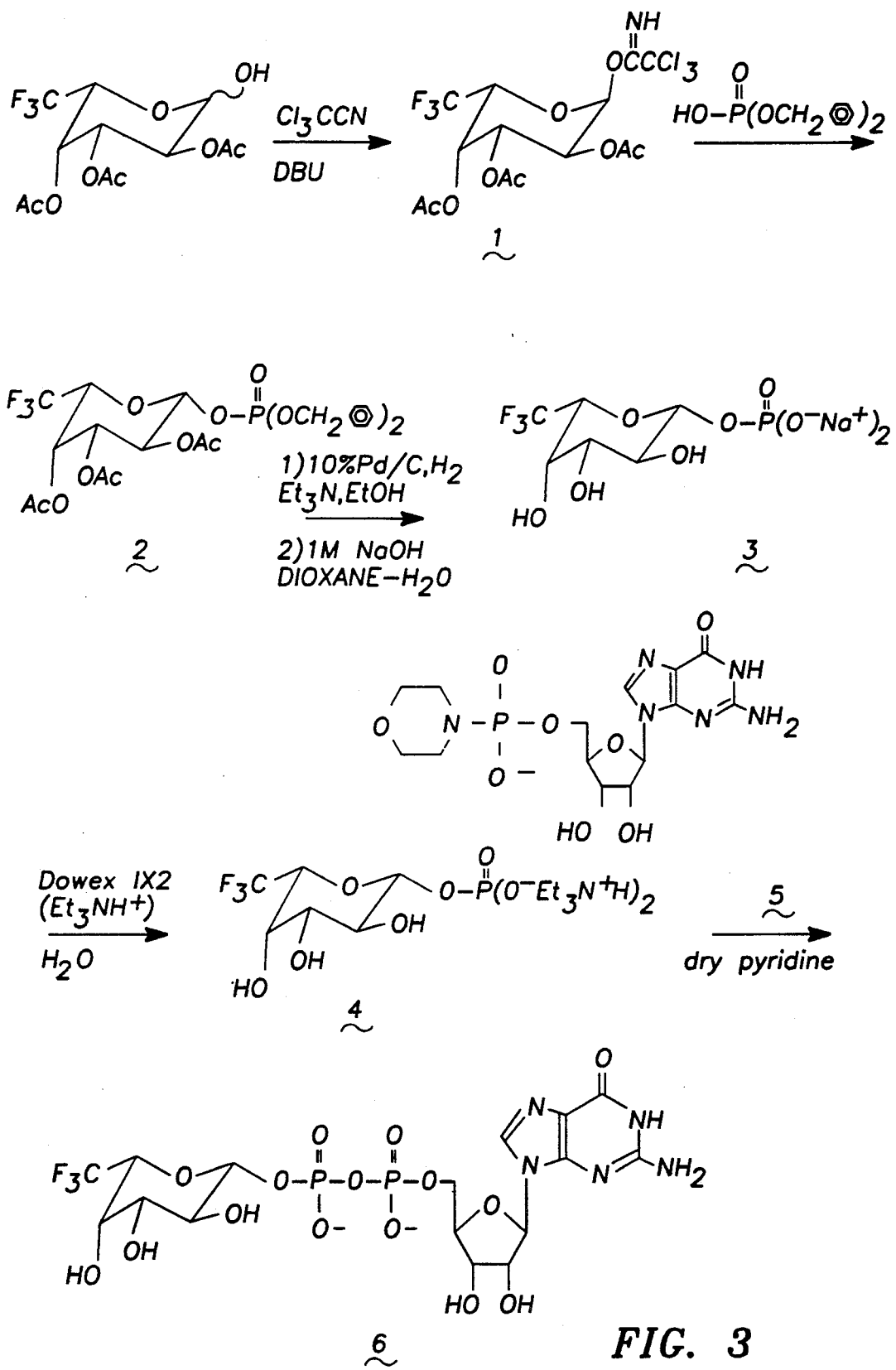
FIG. 3 depicts a flowchart illustrating a procedure for the synthesis of trifluorofucose-GDP.

The synthetic scheme shown in FIG. 3 is based on the published procedure for the synthesis of GDP-fucose (Schmidt et al., Liebigs Ann. Chem. 121, 1991). Trifluorofucose hemiacetal, according to Example 2, is treated with trichloroacetonitrile in the presence of DBU in dichloromethane to give thermodynamically more stable α-trichloroimidate 1 selectively. Phosphorylation of 1 is readily carried out by treatment with dibenzyl phophate in dichloromethane without using any catalyst to yield predominantly β-phophate 2. A sequential deprotection of 2 (i. 10% Pd/C, H$_2$ (1 atm), Et$_3$N, EtOH; ii. 1M NaOH, aq. dioxane) produces a disodium salt of trifluorofucose β-phosphate (3) which is converted to its triethylamine salt 4, by passing through a column of Dowex 1×2 (Et$_3$NH+) with water as an eluent, in order to increase its solubility in organic solvents. The triethylamine salt 4 is then coupled to GMP morpholidate (5) (Sigma, St. Louis, Mo.) in dry pyridine to give a trifluorofucose-GDP conjugate 6, after purification by HPLC (C18) using triethylammonium hydrogen carbonate as a buffer solution.

From the foregoing, it will be evident that, although specific embodiments of the invention have been described herein for purposes of illustration, various modifications may be made without deviating from the spirit and scope of the invention.

We claim:

1. A compound having the formula:

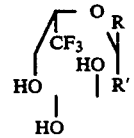

wherein R and R' are H or OH, but are not both H or both OH.

2. A method for the synthesis of 6,6,6-trifluorofucose comprising the steps of:
   (a) reacting a perbenzylated acyclic aldehyde derivative of lyxose with trifluoromethyltrimethylsilane to form trifluoromethylated siloxy adducts of lyxose;
   (b) hydrolyzing said siloxy adducts with about 1M hydrochloric acid to form desilylated adducts;
   (c) reducing said desilylated adducts by catalytic hydrogenation with palladium hydroxide to form deperbenzylated alcohols;
   (d) subjecting said alcohols to pertrimethylsilylation to form trimethylsiloxy adducts;
   (e) oxidizing said trimethylsiloxy adducts with (CrO$_3$-pyridine complex) to form trimethylsiloxy aldehydes;
   (f) desilylating said trimethylsiloxy aldehydes to form a mixture of 6,6,6-trifluorofucose and 6-deoxy-6,6,6-trifluoroaltrose; and
   (g) recovering said 6,6,6-trifluorofucose.

3. A trifluorofucose analog of a fucose-containing oligosaccharide comprising an oligosaccharide selected from the group consisting of Le$^x$, sialyl Le$^x$, disialyl Le$^x$, dimeric Le$^x$, sialyl-dimeric Le$^x$, trifucosyl Le$^x$, and Le$^y$, wherein at least one of the fucoses has been substituted with 6,6,6-trifluorofucose.

4. A composition comprising an oligosaccharide according to claim 3 in combination with a pharmaceutically acceptable carrier or diluent.

5. A trifluorofucose analog of a fucose-containing oligosaccharide, wherein at least one of the fucoses has been substituted with 6,6,6-trifluorofucose.

6. A composition comprising an oligosaccharide according to claim 5 in combination with a pharmaceutically acceptable carrier or diluent.

* * * * *

UNITED STATES PATENT AND TRADEMARK OFFICE
CERTIFICATE OF CORRECTION

PATENT NO. : 5,210,078
DATED : May 11, 1993
INVENTOR(S) : Tatsushi Toyokuni and Sen-itiroh Hakomori It is certified that error appears in the above-indentified patent and that said Letters Patent is hereby corrected as shown below:

In column 10, claim 1, please delete:

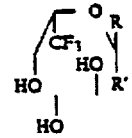

and substitute therefor:

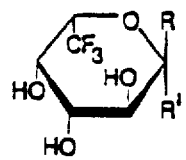

In column 10, claim 2, line 41, after "adducts with" and before "($CrO_3$-pyridine complex)", please insert --Collins reagent--.

Signed and Sealed this

Eighteenth Day of January, 1994

Attest:

BRUCE LEHMAN

Attesting Officer     Commissioner of Patents and Trademarks